US005290219A

United States Patent [19]

Hetrick

[11] Patent Number: 5,290,219

[45] Date of Patent: Mar. 1, 1994

[54] THERAPY MACHINE

[76] Inventor: Beryl W. Hetrick, 160 Fisher Ct., Calimesa, Calif. 92320

[21] Appl. No.: 983,397

[22] Filed: Nov. 30, 1992

[51] Int. Cl.[5] .............. A61F 5/00

[52] U.S. Cl. .............. 602/32; 602/33; 5/83.1; 5/85.1; 601/35

[58] Field of Search .............. 5/83.1-87.1; 602/32-36; 128/25 R, 25 B, 25 C, 26, 75; 606/241

[56] References Cited

U.S. PATENT DOCUMENTS

| | | | |
|---|---|---|---|
| 935,170 | 9/1909 | Smith | 5/86.1 |
| 2,183,265 | 12/1939 | Maloney . | |
| 2,315,997 | 4/1943 | Ginsberg . | |
| 2,374,163 | 4/1945 | Burchsted | 602/32 |
| 2,631,582 | 3/1962 | Bensfield . | |
| 3,403,675 | 10/1968 | Carr | 602/32 |
| 3,623,480 | 11/1971 | Chisolm | 128/25 R |
| 3,683,898 | 8/1972 | Underwood . | |
| 3,693,614 | 9/1972 | Schon . | |
| 3,877,421 | 4/1975 | Brown . | |
| 4,003,479 | 1/1977 | Reyer | 5/86.1 |
| 4,282,865 | 8/1981 | Pogue . | |
| 4,372,452 | 2/1983 | McCord | 5/85.1 |

*Primary Examiner*—Richard J. Apley
*Assistant Examiner*—Jeanne Mollo
*Attorney, Agent, or Firm*—Sheldon & Mak

[57] ABSTRACT

An apparatus for exercising a bed-ridden patient includes a frame; a load movably supported by the frame and having a load attachment point for movably carrying a limb of the patient, the load including a wheeled carriage, the frame including a track for guiding the carriage; a drive for repetitively cycling the load in a carriage path relative to the frame and including a first crank driven by a motor, and a first connecting rod pivotally connected to the first crank for reciprocating the carriage along the track; a base for supportively anchoring the apparatus; a pivot for adjustably orienting the frame in a fixed position relative to the base, the pivot having a first position for horizontally orienting the track for lateral movement of the limb and a second position for vertically orienting the track for raising and lowering the limb; and a base plate, the frame being supported by the base plate, the lift attachment point being fixably located relative to the base plate, a clamp arm pivotally connected between the clamp and the base plate, and a clamp lock for fixably locating the clamp arm in a plurality of angular orientations relative to the base plate.

14 Claims, 2 Drawing Sheets

THERAPY MACHINE

BACKGROUND

The present invention relates to physiotherapy, and more particularly to apparatus for mechanically exercising the muscles and joints of a patient's body.

Machines and other devices for manipulating the limbs of bedridden and otherwise physically impaired patients are known. For example, U.S Pat. No. 2,183,265 to Maloney discloses a rope having a sling at one end and a hand grip on the other, the rope being movably supported by a ceiling-mounted pulley for raising a patient's legs when the patient pulls downwardly on the hand grip, a releasable catch holding the legs in an elevated position. U.S. Pat. No. 2,631,582 to Bensfield discloses a portable adjustable manipulating apparatus, the apparatus including a U-shaped frame disposed on its side, a standard projecting up from one end of the carriage, and an arm projecting horizontally from the upper end of the standard for overlying the carriage. The carriage can be inserted beneath a bed so that the standard projects upwardly at an edge or end of the bed, thus positioning the arm over the bed. The carriage includes motor which operates a crank at variable speeds. A sling for holding a patient's limb is attached to a line which is operated by the crank. Adjustable and traveling blocks vertically movable within the standard provide an adjustable stroke of the line. U.S. Pat. No. 3,683,898 to Underwood discloses a therapeutic apparatus including an exercise bar supported above a bed by a block and tackle assembly. The block and tackle assembly is connected with a motor for reciprocating the bar vertically. The bar is also supported and optionally driven for angular displacements about a generally vertical axis. U.S. patent No. 3,693,614 to Schon patent discloses an exercise apparatus including a support beam attached to the frame of a patient's bed by a vertical post. A motor driven pedal device is adjustably affixed to the beam, the pedal device having a pair of crank arms attached to opposite ends of a drive spindle, outwardly extending pedal rods being attached to the free end of each crank arm. The apparatus includes a pair of support plates designed to be affixed to the patient's shoes and another pair of support plates designed to be affixed to gloves for the patient's hands. The patient's hands or feet can be thus attached to the pedal device by slipping the tubular portion of the support plates over the pedal rods. An upwardly extending leg supports a pair of extension springs that biasingly support corresponding leg straps. U.S. Pat. No. 4,282,865 to Pogue discloses an apparatus for exercising a limb of a supine user, including a housing, a movable member on the housing for engaging an extremity of the limb, and a drive mechanism on the housing for reciprocating and/or oscillating the movable member on an adjustably inclined axis for exercising the user's limb in a generally horizontal, longitudinal direction.

These and other prior art devices are subject to one or more of the following disadvantages:

1. They are so bulky and unwieldy that they are impractical for use in confined spaces that are typically available at hospital and home bed locations, especially in view of other equipment that is likely to be needed for the patient;

2. They are limited in application in that they are capable of movement in a single direction only, at a fixed speed, and/or through an unchangeable distance; and 3. They are mechanically cumbersome and complicated, being difficult to use and expensive to produce.

Thus there is a need for a device for manipulating the limbs of patients that may be bedridden or otherwise physically impaired, that overcomes the above disadvantages.

SUMMARY

The present invention meets this need by providing an apparatus for exercising a bed-ridden patient. In one aspect of the invention, the apparatus includes a frame; a load member movably supported by the frame and having a load attachment point for movably carrying a limb portion of the patient; drive means for repetitively cycling the load member in a carriage path relative to the frame; base means for supportively anchoring the apparatus; and pivot means for adjustably orienting the frame in a fixed position relative to the base means.

The load member can include a wheeled carriage, the frame including track means for rollably guiding the carriage. The drive means can include a first crank member and motor means for driving the first crank member, and a first rigid connecting rod pivotally connected to the first crank member for reciprocating the carriage along the track means. The connecting rod can be adjustably connected to the first crank member for adjusting a travel distance of the load member.

The pivot means can have a first position for horizontally orienting the track means for lateral movement of the limb portion and a second position for vertically orienting the track means for raising and lowering the limb portion. The frame can be pivotally mounted on a horizontal axis for movement between the first and second positions of the pivot means. The base means can include a clamp member for clamping to an external hoist arm. Preferably the base means further includes a lift attachment point for supportively connecting a lift extremity of the hoist arm, the clamp member being spaced from the lift attachment point. The frame can be supported by a base plate, the lift attachment point being fixably located relative to the base plate, a clamp arm pivotally connected between the clamp member and the base plate, and clamp lock means for fixably locating the clamp arm in a plurality of angular orientations relative to the base plate.

A driven portion of the limb can be suspended from the load attachment point, the apparatus further including auxiliary support means fixably located relative to the frame for supporting the limb at a location spaced apart from the driven portion. The auxiliary support means can include an auxiliary arm and socket means on the frame for holding an end of the arm. The socket means can include a pair of socket members at opposite sides of the frame for selectively locating the auxiliary arm on opposite sides of the load attachment point.

DRAWINGS

These and other features, aspects, and advantages of the present invention will become better understood with reference to the following description, appended claims, and accompanying drawings, where:

DESCRIPTION

Figure 1:
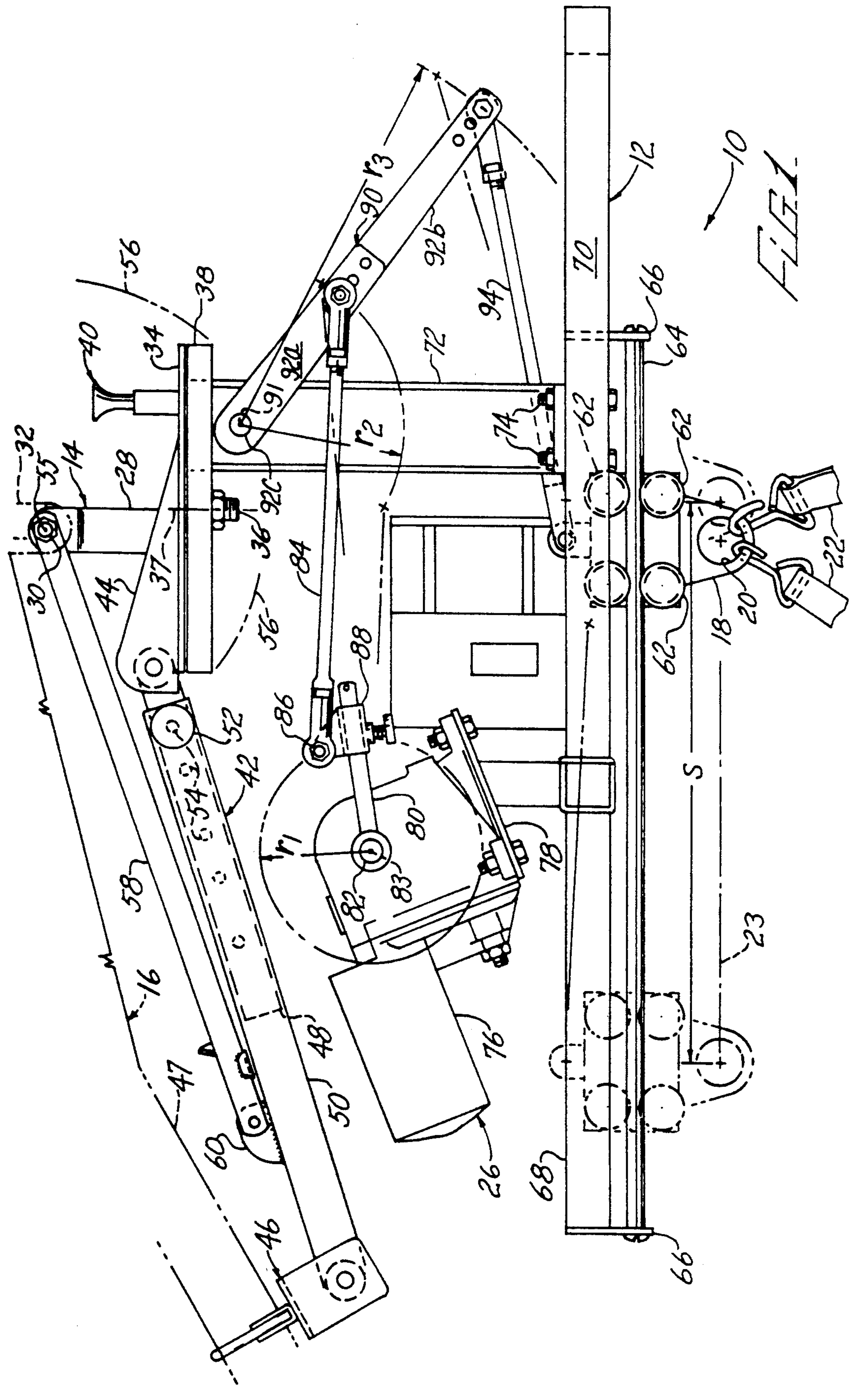
FIG. 1 is a side elevational view of a therapy machine according to the present invention.
Figure 2:
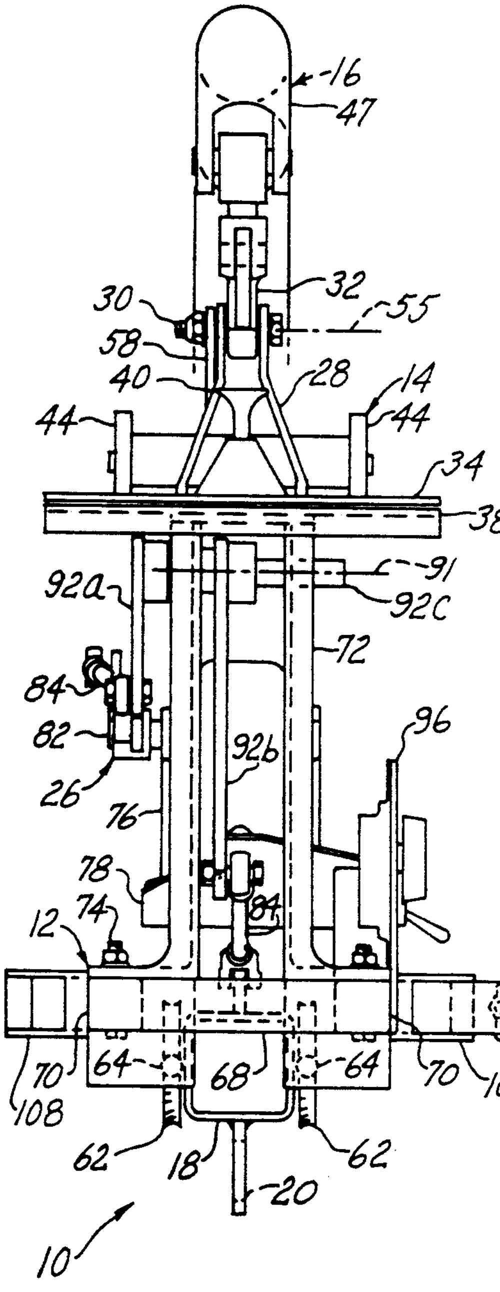
FIG. 2 is an end elevational view of the machine of FIG. 1.

The present invention is directed to a physiotherapy machine that is particularly versatile, effective and easy to use in both hospital and home environments. With reference to FIGS. 1-4 of the drawings, a machine 10 according to the present invention includes a frame 12, and index means 14 for adjustably supportively positioning the frame 12 relative to a conventional hoist or lift 16. A carriage 18 that is movably supported relative to the frame 12 has a load point 20 for supporting one or more straps 22, the load point 20 being movable along a drive path 23. The straps 22 are connectable to a limb 24 of a bed-occupying patient 25, the machine 10 further including drive means 26 for adjustably cycling the carriage 18, whereby the limb 24 is therapeutically manipulated by movement of the load point 20 along the drive path 23 for treating the patient 25.

The index means 14 includes a hanger 28 having a laterally disposed attachment bolt 30 for connection to a latch clip 32 of the lift 16 the hanger 28 being fixably mounted to a platform member or latch 34. The latch plate 34 is rotatably connected by a fastener 36 to an index plate 38 that forms a part of the frame 12, the fastener 36 defining an index axis 37 that is perpendicular to the attachment bolt 30. An axially movable latch 40 is mounted on the latch plate 34 for selectively engaging one of a plurality of index holes 41 of the index plate 38, thereby locking the index plate 38 in a desired rotational orientation about the index axis 37 relative to the latch plate 34.

Figure 3:
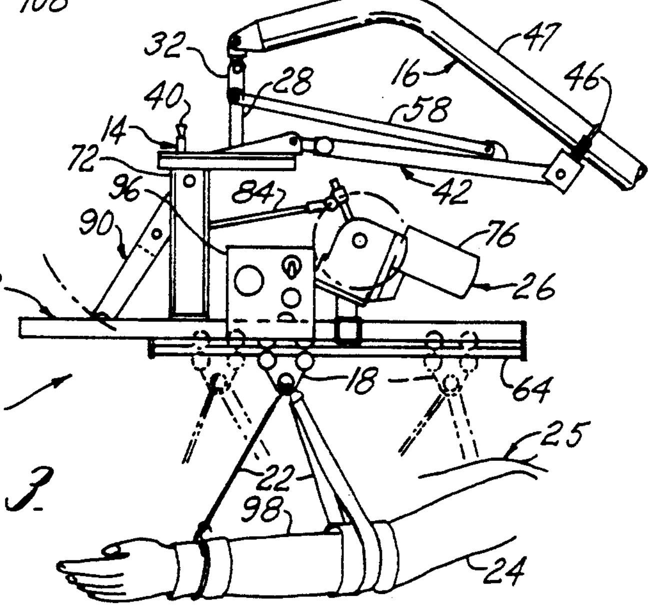
FIG. 3 is a side elevational view of the machine of FIG. 1 in use on a hospital lift for horizontally exercising a patient's arm.

The index means 14 also includes an adjustably extendable arm assembly 42, one end thereof being pivotally mounted between a pair of arm blocks 44 that are fixably mounted to the latch plate 34, the opposite end of the arm assembly 42 being pivotally connected to a clamp assembly 46 that is rigidly connectable to a hoist arm 47 of the lift 16 in spaced relation to the latch clip 32, the clip 32 defining a lift extremity of the hoist arm 47 as best shown in FIG. 3. The arm assembly 42 includes a telescopic pair of arm members, designated inner arm 48 and outer arm 50, an arm latch 52 that is mounted on the outer arm 50 selectively engaging a spaced plurality of openings 54 in the inner arm 48 for locking the frame 12 in a desired angular position about a horizontal pivot axis 55 relative to the hoist arm 47 of the lift 16, as indicated by the dashed lines 56 in FIG. 1. A stabilizing link 58 is also pivotally connected between the attachment bolt 30 and an upstanding tab member 60 that is rigidly positioned on the outer arm 50. The stabilizing link 58 serves to facilitate proper location of the clamp assembly 42 on the hoist arm 47 when mounting the machine 10 on the lift 16, and to prevent free swinging movement of the latch clip 32 once the clamp assembly 46 has been tightened in place. The pivot axis 55 is concentric with the attachment bolt 30. It will be understood that adjustment of the arm assembly 42 does produce very slight movement of the latch clip 32, and corresponding movement of the pivot axis 55, as the stabilizing link 58 pivots relative to the outer arm 50. However, the location of pivot axis 55 and the angular orientation of the latch plate 34 are fixed by the adjustment of the arm assembly 42. Thus the latch plate 34 provides an adjustably oriented fixed base for the frame 12.

The carriage 18 has four pairs of concavely-rimmed rollers 62 that guide the carriage 18 along a pair of cylindrical rails 64, the rails 64 being rigidly supported relative to the frame 12 by a pair of rail plates 66 that fixably connect a base portion 68 of the frame 12. The base portion 68, in an exemplary configuration of the machine 10, is formed from aluminum tubing of square cross-section as an elongate U-shaped weldment, the rail plates 66 being spaced apart in perpendicular relation to side members 70 of the base portion 68. A pair of risers 72 rigidly connect the index plate 38 in parallel-spaced relation to the side members 70 of the base portion 68 of the frame 12, using fasteners 74.

The drive means 26 includes a reduction-geared motor 76 that is mounted to an inclined platform 78, the platform 78 forming a rigid extension of the base portion 68 of the frame 12. A drive arm 80 is rigidly mounted to a motor shaft 82 of the motor 76 for rotation on a motor axis 83, one end a first drive link 84 being pivotally connected to the arm 80 through a drive journal 86 that is adjustably clampable relative to the arm 80, at a distance $r_1$ from the axis 83, by a drive clamp 88. The opposite end of the first drive link 84 is pivotally connected to a compound arm 90 that is pivotally movable on an arm axis 91 relative to the frame 12. The compound arm 90 includes a relatively short driven member 92*a* to which the link 84 is connected at a distance $r_2$ from the arm axis 91, a longer driver member 92*b*, and a shaft member 92*c*, shaft member 92*c* being rigidly connected to the members 92*a* and 92*b* and rotatably supported between the risers 72 (on the arm axis 91. A second drive link 94 is pivotally connected between the driver member 92*b* (at a distance $r_3$ from the arm axis 91) and the carriage 18 for repetitively moving the carriage 18 along the rails 64. The drive arm 80, the compound arm 90, and the drive links 84 and 94 are configured and located relative to the frame 12 for bidirectionally moving the carriage 18 and the load point 20 a distance S along the drive path 23 during each revolution of the motor shaft 82. The distance S is approximately equal to $2*r_1*r_3/r_2$.

The machine 10 also includes a control panel 96 that is mounted to the frame 12 and electrically connected to the motor 76 for variable speed control thereof in a conventional manner.

As shown in FIG. 3, the index means 14 is operative for locking the frame 12 with the rails 64 horizontally disposed over the patient 25 when the machine 10 is supported on the lift 16. In this configuration of the index means 14, the drive path 23 is horizontally oriented for generally horizontal movement of the limb 24, the limb 24 being shown as an arm 98 of the patient 25. In further accordance with the present invention, the latch 40, in combination with the latch plate 34, the fastener 36, and the index plate 38, permits the lift 16 to be located at either side or an end of a bed (not shown) that supports the patient 25, the rails 64 being aligned in a desired horizontal direction. Moreover, when the rails 64 are oriented at angles other than perpendicular to a vertical plane occupied by the lift 16, an inclined path for the carriage 18 can be defined by adjustment of the arm assembly 42 which produces a corresponding inclination of the rails 64.

Figure 4:
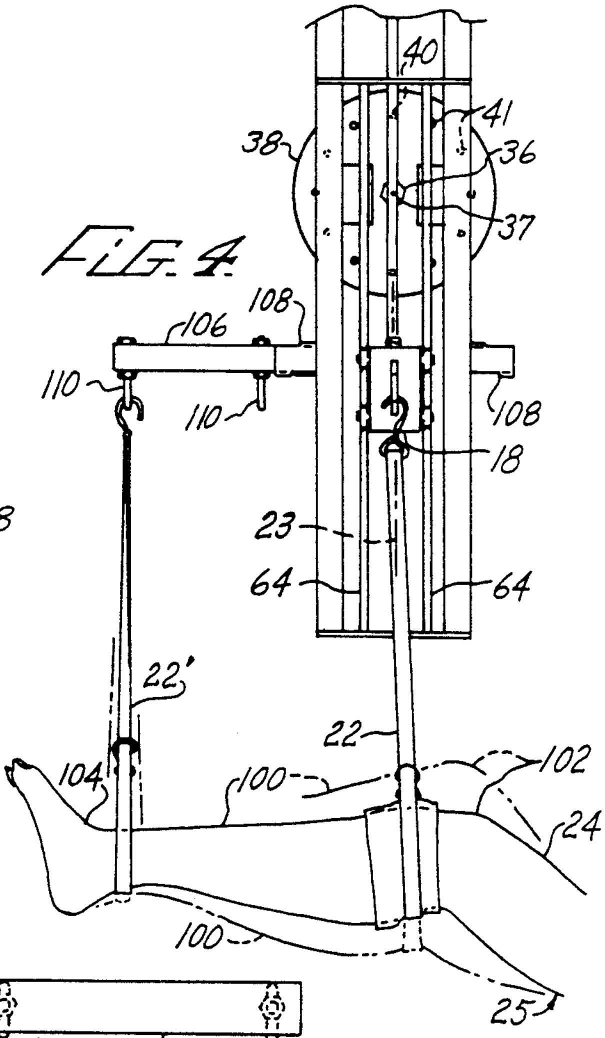
FIG. 4 is a side elevational view of the machine of FIG. 1 in use for vertically exercising a leg of the patient.

As further shown in FIG. 4, adjustment of the arm assembly 42 permits the latch plate 34 to be locked in a vertical plane, the rails 64 also being intersected by a vertical plane. In the configuration of FIG. 4, the index plate 38 is also rotationally oriented about the index axis 37 such that the rails 64 are vertically oriented for correspondingly vertically orienting the drive path 23. This configuration of the machine 10 advantageously provides vertical exercise of the patient's limb 24, the limb 24 being shown as a leg 100 of the patient 25. More particularly, the strap 22 is shown supporting the leg 100 just below the knee (designated 102) for vertical movement thereof. A counterpart of the strap 22, designated 22', is shown supporting a foot portion 104 of the limb 24 vertically stationary, the strap 22' being suspended from an auxiliary arm 106 that removably engages the frame 12. The base portion 68 of the frame 12 is provided with a pair of oppositely projecting sockets 108 for holding one end of the auxiliary arm 106, so that the strap 22' is supportable laterally spaced from a selected side of the drive path 23. Thus the machine 10 can be used with the straps 22 and 22' supporting respective knee and foot locations of the leg 100, with the lift 16 situated at either side of the patient 25. A spaced pair of hangers 110 are provided on the auxiliary arm 106 for permitting the strap 22' to be anchored at a selectable distance from the drive path 23.

Although the present invention has been described in considerable detail with reference to certain preferred versions thereof, other versions are possible. For example, the drive path 23 can be made curved by curving the rails 64, or by locating the load point 20 on a counterpart of the compound arm 90. Further, the compound arm 90 can form part of a linkage that supports the load point. Therefore, the spirit and scope of the appended claims should not necessarily be limited to the description of the preferred versions contained herein.

What is claimed is:

1. Apparatus for exercising a bed-ridden patient, comprising:
   (a) a frame;
   (b) a load member assembly supported relative to the frame and having a load attachment point for movably carrying a limb portion of the patient;
   (c) drive means for repetitively cycling the load member in a carriage path relative to the frame;
   (d) base means for supportively anchoring the apparatus; and
   (e) pivot means for adjustably orienting the frame in a fixed position relative to the base means, the pivot means moves the frame in a first position for horizontally orienting the carrying path for lateral movement of the limb portion and moves the frame in a second position for vertically orienting the carriage path for raising and lowering the limb portion.

2. The apparatus of claim 1, wherein the load member comprises a wheeled carriage for movement along the carriage path, the frame including track means for rollably guiding the carriage.

3. The apparatus of claim 2, wherein the drive means comprises a first crank member and motor means for driving the first crank member, and a first rigid connecting rod pivotally connected to the first crank member for reciprocating the carriage along the track means.

4. The apparatus of claim 3, wherein the connecting rod is adjustably connected to the first crank member for adjusting a travel distance of the load member.

5. The apparatus of claim 1, wherein the frame is pivotally mounted on a horizontal axis for movement between the first and second positions of the pivot means.

6. The apparatus of claim 5, wherein the base means comprises a clamp member for clamping to an external hoist arm.

7. The apparatus of claim 6, wherein the base means further comprises a lift attachment members for supportively connecting a lift extremity of the hoist arm, the clamp member being spaced from the lift attachment member.

8. The apparatus of claim 7, further comprising a platform member, the frame being supported by the platform member, the lift attachment member being fixably located relative to the platform member, a clamp arm pivotally connected between the clamp member and the platform member, and clamp lock means for fixably locating the clamp arm in a plurality of angular orientations relative to the platform member.

9. The apparatus of claim 8, wherein the frame comprises an index member, the index member being pivotally connected to the platform member on an index axis, the index axis being inclined relative to the horizontal axis of movement between the first and second positions of the pivot means.

10. The apparatus of claim 9, wherein the index axis is perpendicular to the horizontal axis.

11. The apparatus of claim 1, wherein the load attachment point comprises means for supporting a driven portion of the limb of the patient from the load attachment point, the apparatus further comprising auxiliary support means fixably located relative to the frame for supporting the limb at a location spaced apart from the driven portion.

12. The apparatus of claim 11, wherein the auxiliary support means comprises an auxiliary arm and socket means on the frame for holding an end of the arm.

13. The apparatus of claim 11, wherein the socket means comprises a pair of socket members at opposite sides of the frame for selectively locating the auxiliary arm on opposite sides of the load attachment point.

14. Apparatus for exercising a bed-ridden patient, comprising:
   (a) a frame;
   (b) a load member movably supported by the frame and having a load attachment point for movably carrying a limb portion of the patient, the load member comprising a wheeled carriage, the frame including track means for rollably guiding the carriage;
   (c) drive means for repetitively cycling the load member in a carriage path relative to the frame, the drive means comprising:
      (i) a first crank member and motor means for driving the first crank member; and
      (ii) a first rigid connecting rod pivotally connected to the first crank member for reciprocating the carriage along the track means;
   (d) base means for supportively anchoring the apparatus, comprising a clamp member for clamping to an external hoist arm, and a lift attachment member for supportively connecting an extremity of the hoist arm;
   (e) pivot means for adjustably orienting the frame in a fixed position relative to the base means, the pivot means having a first position for horizontally orienting the track means for lateral movement of the limb portion and a second position for vertically orienting the track means for raising and lowering the limb portion;

(f) a platform member, the frame being supported by the platform member, the lift attachment member being fixably located relative to the platform member, a clamp arm pivotally connected between the clamp member and the platform member, and clamp lock means for fixably locating the clamp arm in a plurality of angular orientations relative to the platform member.

* * * * *